US006409661B1

(12) United States Patent
Murphy

(10) Patent No.: US 6,409,661 B1
(45) Date of Patent: Jun. 25, 2002

(54) DIAGNOSTIC APPARATUS

(75) Inventor: Graham Francis Murphy, Alresford (GB)

(73) Assignee: Remote Diagnostic Technologies Limited, Basingstoke (GB)

( * ) Notice: Subject to any disclaimer, the term of this patent is extended or adjusted under 35 U.S.C. 154(b) by 0 days.

(21) Appl. No.: 09/380,724

(22) PCT Filed: Feb. 27, 1998

(86) PCT No.: PCT/GB98/00613

§ 371 (c)(1),
(2), (4) Date: Dec. 21, 1999

(87) PCT Pub. No.: WO98/40009

PCT Pub. Date: Sep. 17, 1998

(30) Foreign Application Priority Data

Mar. 8, 1997 (GB) .............................. 9704843

(51) Int. Cl.[7] .............................. A61B 5/00
(52) U.S. Cl. ..................................... 600/300
(58) Field of Search ................. 600/300, 301; 607/5; 395/839; 361/704; 379/106.02; 128/898, 696, 204.23

(56) References Cited

U.S. PATENT DOCUMENTS

| 4,097,691 A | 6/1978 | Ehrlich et al. |
| 4,102,332 A | 7/1978 | Gessman |

(List continued on next page.)

FOREIGN PATENT DOCUMENTS

| EP | 0535629 A1 | 9/1992 |
| EP | 0707824 A2 | 4/1996 |
| EP | 0710465 A1 | 5/1996 |
| GB | 2259772 A | 3/1993 |
| GB | 2285135 A | 6/1995 |
| GB | 2288511 A | 10/1995 |
| WO | 83/01374 | 4/1983 |
| WO | 94/10902 | 5/1994 |
| WO | WO 94/24929 | 11/1994 |

OTHER PUBLICATIONS

Mark Ward, "Flight plans for Doc–in–a–box", New Scientist, Jun. 1996, p24.
Mariette DiChristina, "Doctor in the Sky", Popular Science, 1995, p. 50.
International Search Report.

*Primary Examiner*—John P. Lacyk
*Assistant Examiner*—Brian Szmal
(74) *Attorney, Agent, or Firm*—Ratner & Prestia

(57) ABSTRACT

Medical sensors (1 to 4) are connected to a processor (6) comprising a PC and modems (14 and 16). The modems are connected to respective low power transmitter/receivers (18 and 20) The transmitter/receivers (18, 20) communicate with corresponding receiver/transmitters (18', 20') connected to a long range transmitter/receiver such as a satellite communications link (22, 23, 24). An operator of the apparatus has a hands free headset comprising a microphone (7) and earpieces (8), and has a head-up display (10). An electronic camera may also be provided. Medical data from the sensors (1–4) and images from the camera (9) and voice signals from the microphone (7) are processed by the processor (6), and transmitted to a remote location (B), for use by a doctor having a corresponding processor and display to diagnose the condition of a patient. The doctor can talk to the operator to advise on the condition and treatment of the patient.

42 Claims, 5 Drawing Sheets

U.S. PATENT DOCUMENTS

| | | |
|---|---|---|
| 4,173,971 A | 11/1979 | Karz |
| 4,356,486 A | 10/1982 | Mount |
| 4,838,275 A | 6/1989 | Lee |
| 4,958,645 A | 9/1990 | Cadell et al. |
| 5,333,616 A | 8/1994 | Mills et al. |
| 5,348,008 A * | 9/1994 | Bornn et al. ............... 128/642 |
| 5,381,798 A | 1/1995 | Burrows |
| 5,417,222 A | 5/1995 | Dempsey et al. |
| 5,441,047 A | 8/1995 | David et al. |
| 5,462,051 A | 10/1995 | Oka et al. |
| 5,467,773 A | 11/1995 | Bergelson et al. |
| 5,522,396 A | 6/1996 | Langer et al. |
| 5,544,649 A | 8/1996 | David et al. |
| 5,544,661 A | 8/1996 | Davis et al. |
| 5,579,001 A | 11/1996 | Dempsey et al. |
| 5,579,775 A | 12/1996 | Dempsey et al. |
| 5,586,556 A | 12/1996 | Spivey et al. |
| 5,619,991 A | 4/1997 | Sloane |
| 5,687,734 A | 11/1997 | Dempsey et al. |
| 5,704,364 A * | 1/1998 | Saltzstein et al. ........... 128/696 |
| 5,792,190 A * | 8/1998 | Olson et al. .................... 607/5 |
| 5,878,276 A * | 3/1999 | Aebli et al. ................. 395/839 |
| 5,950,632 A * | 9/1999 | Reber et al. ................. 128/898 |
| 5,974,124 A * | 10/1999 | Schlueter, Jr. et al. .. 379/106.02 |
| 6,058,012 A * | 5/2000 | Cooper et al. .............. 361/704 |
| 6,135,107 A * | 10/2000 | Mault .................... 128/204.23 |

\* cited by examiner

DIAGNOSTIC APPARATUS

FIELD OF THE INVENTION

The present invention relates to diagnostic apparatus.

A preferred embodiment of the invention as described herein is for use in aircraft for the diagnosis of medical emergencies, on aircraft in flight, of humans. However, the invention is not limited to that. The medical diagnostic apparatus may be useful on animals, especially mammals. The medical diagnostic apparatus may be used on other vehicles, e.g. ships, and may be useful on land especially in locations remote from medical help.

BACKGROUND

U.S. Pat. No. 5441047 (DAVID et al) discloses a patient health monitoring system for use in homes of patients. A two-way audio and video (A/V) link is established between the patients home and a remote care centre using a camera and a standard TV set in the home linked by e.g. a cable television network to a monitor and camera respectively in the care centre. In addition a plurality of medical sensors for sensing medical data of the patient are provided in the home, for example in a special chair in which the patient sits, and linked by a monitor equipment including a modem and a telephone line to the care centre. The monitor equipment may have a display for displaying the sensed medical data: the camera may be used to view the display instead of transmitting the data via the telephone line. A nurse in the care centre examines the medical data. The nurse and the patient can see each other and talk to each other via the A/V link. The A/V link could be via modem through telephone lines. The video signal and/or the medical data may be transmitted by satellite and/or radio transmission.

WO 94/24929 (HEALTHDYNE, INC.) disclose a patient monitoring and support system for monitoring a plurality of patients located at locations remote from a care centre. At each patient site, there is a base unit, which can be connected to a plurality of sensors for producing medical data relating to the patient's medical state. The base unit stores the medical data and transfers it to the care centre where it is stored and analysed. Care providers at the centre monitor the patients. The base unit comprises a housing containing, inter alia, the medical sensors, an IBM compatible personal computer, an LCD display and a modem for transferring data to and from the care centre via a telephone line. The LCD display displays sensed medical data and instructions to the patient on the use of the monitoring system. A standard telephone set may be connected to the telephone line.

SUMMARY OF THE INVENTION

According to the present invention there is provided Diagnostic Apparatus comprising:

a plurality of sensing means for sensing data of a body;

means for producing and reproducing voice signals, the producing and reproducing means being arranged to be used by an operator hands-free;

a first communications means coupled to the producing and reproducing means, and a second communications means;

display means; and processing means arranged to i) process the sensed data, ii) display the processed data on the display means, iii) control the first and second communications means to automatically establish respective links to a remote location, and iv) supply the processed data to the second communications means;

the apparatus being arranged so that in use two-way voice communication is established between the said operator and an expert at the remote location and the sensed data is transferred to the remote location via the second communications link to allow the said expert to diagnose the condition of the body and to communicate the diagnosis to the said operator.

Preferably, the apparatus is a medical diagnostic apparatus, the body is that of a human and the expert is a medical expert. The invention and the embodiments will be discussed hereinafter and by way of example to such medical diagnostic apparatus.

The apparatus according to the invention, thus integrates the elements of the apparatus into a single system controlled by the processor (unlike the system of David et al), and automatically establishes both two-way voice communication with, and simultaneous data transfer to, the remote location (unlike the system of Healthdyne) providing ease of use with a minimum of involvement by the operator and of swift access in an emergency to medical advice based on an analysis of the transferred medical data.

In a preferred embodiment of the invention, the apparatus is portable. Most preferably the whole portable apparatus is housed in a container.

In a preferred embodiment of the invention the data and voice signals are arranged to be transferred via the Public Switched Telephone Network (PSTN). In the currently preferred embodiment the processor is arranged to auto-dial the remote location once the operator has initiated the auto-dial function of the apparatus.

In an embodiment of the invention, ease of use is enhanced by providing a head-up display for displaying the processed medical data to the operator and preferably also for displaying instructions on the operation of the apparatus. An additional display, e.g. an LCD display panel, is preferably provided to allow an assistant to view the processed data and the operating instructions.

Preferably the apparatus is arranged to automatically 'boot-up' to its operating state automatically on power-up without intervention by the operator.

Preferably the operator is provided with a simplified key-pad (instead of a full keyboard) with the minimum of keys needed to operate the apparatus. The key-pad may be worn on the wrist like a watch. A full keyboard is unnecessary for operating the apparatus and would take up unnecessary space which may be severely restricted such as in an aircraft.

Preferably, a camera is provided to produce images to aid diagnosis. The camera is preferably a digital video camera from which the processing means grabs still images for transmission to the remote location. The camera may be strapped to the wrist of the operator for ease of use.

The said first and second communications means may be low-power wireless transmitter/receivers such as modified CT2, DECT, or spread-spectrum (such as CDMA) cordless phones which communicate over a short distance and which are linked to long range communications channels. In for example a large aircraft, a cabin telephone unit CTU is present. On current aircraft there are telephones on bulkheads or on seat-backs. Such phones are wired to the CTU. The phones have telephone sockets (RJ45 sockets) in them to allow other telephonic equipment to be connected to them. In use of the present apparatus, cordless base stations corresponding to the cordless phones are plugged into the telephone sockets.

Alternatively the first and second communications means are telephone cables which plug into the telephone sockets. Preferably, both cables and low-power wireless transmitter/receivers such as modified CT2 , DECT or CDMA cordless phones are provided and the operator simply plugs the cables into the seat jacks. Most preferably the apparatus comprises means for automatically sensing whether the cables or the low-power wireless transmitter/receivers are operating on the aircraft and for routing the data and voice signals appropriately: this eases the use of the apparatus. The CTU links for example to a satellite communications channel which in turn links to the PSTN. In-flight communications systems other than satellite systems are available and their use is within the scope of the invention.

It is possible that the CTU is a cordless unit. Then the cordless phones may communicate with it direct. Alternatively, appropriate cordless base stations may be installed in the CTU.

The provision of cordless phones allows the apparatus to be used anywhere in the aircraft without the need for long cables. Furthermore, the provision of cordlessphones and the ability to plug cords into any nearby phone on an aircraft allows the diagnostic apparatus to be at the seat of a patient avoiding the need to move the patient.

The medical sensors preferably comprise a 12 lead ECG array, a temperature sensor, a pulse oximeter, a capnometer and a blood pressure monitor. This combination of sensors is currently considered to be adequate to provide reliable diagnosis of most common conditions or at least to determine the seriousness of a medical condition. Other combinations of sensors are within the scope of the invention.

In an embodiment, the processor compresses the ECG data and organises it into files. Likewise the processor organises the image data from the camera into files. Preferably, the processor encodes the image and sensor data into the known internet protocol TCP/IP and uses FTP to transfer the image and ECG data files to the remote location. This facilitates the transfer of the data from the remote location via the internet to other locations if more advice or analysis is needed.

Ease of use is further enhanced in a most preferred embodiment of the invention by containing the apparatus in a container. The container comprises at least one compartment containing the processor and the first and second communications means and at least one other compartment containing at least the sensing means, and the producing and reproducing means. The said at least one other compartment may also contain the head-up display. The container has an openable lid and preferably the said LCD display panel is housed in the lid. Preferably the lid is separable from the container so that the LCD display can be positioned conveniently to be viewed. Preferably the said at least one compartment containing the processor and the communications means is RF screened, the communications means having antennae which extend outside the second compartment. Preferably the base of the container is a heat sink which provides the floor of the said at least one compartment, and at least the processor is thermally coupled to the heat sink. Preferably the apparatus is battery powered, by for example a combination of rechargeable and non-rechargeable batteries and the batteries are contained in a yet further compartment in the container.

The said sensors and the head-up display and the audio head set and the leads therefor are contained in the container which has clearly defined spaces for such items so that they are stored in preset positions and are stored in a way which minimises the risk of damage. Preferably at least the sensors are stored in depressions in the surface of a plastics foam holder.

For a better understanding of the present invention reference will now be made by way of example to the accompanying drawings, in which:

DETAILED DESCRIPTION OF THE EXEMPLARY EMBODIMENTS OF THE INVENTION

Figure 1:
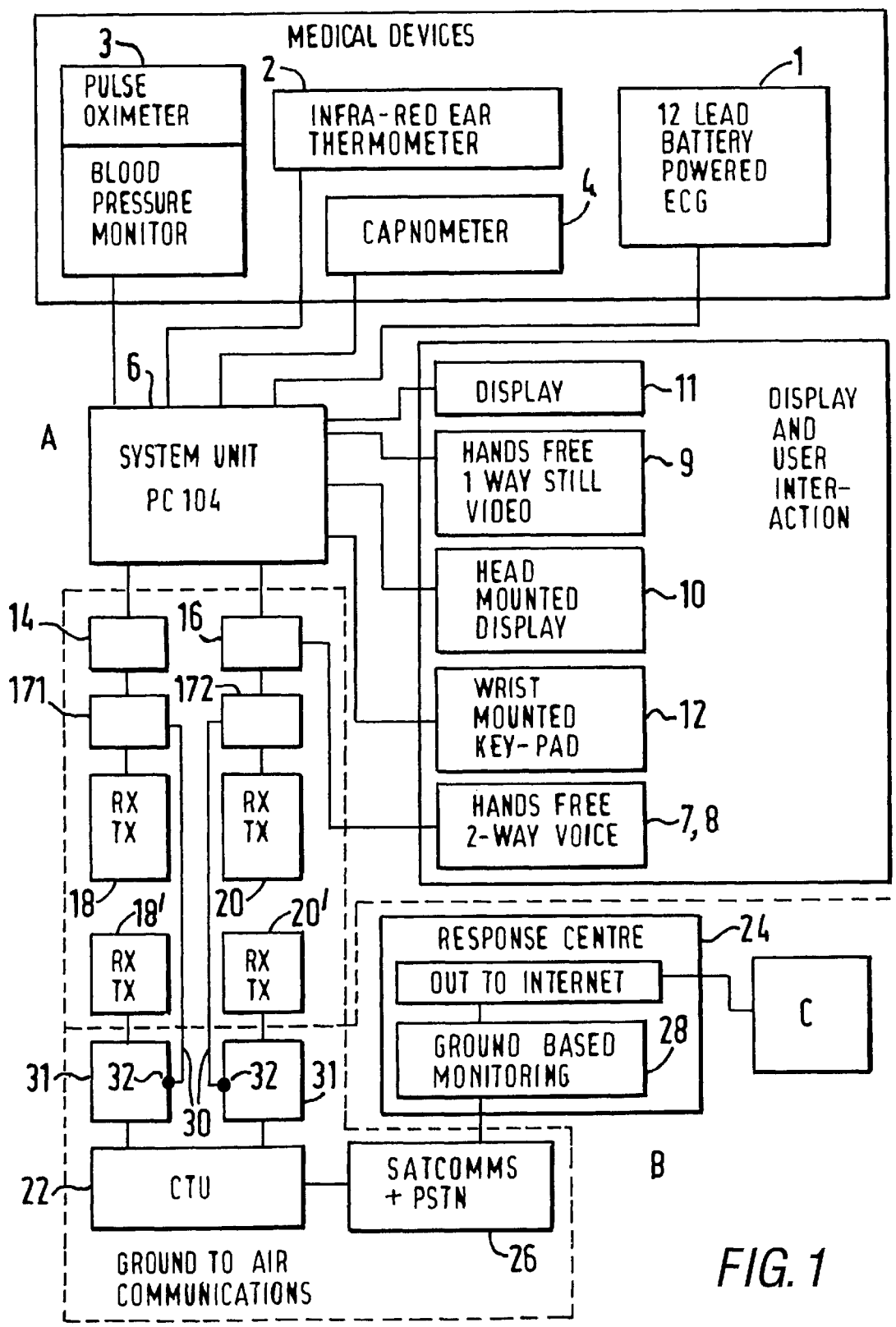
FIG. 1 is a system block diagram of an illustrative medical diagnostic apparatus for use on an aircraft, and a ground-based response centre and a communications system.

The invention will be illustrated by reference to apparatus for use on an aircraft for diagnosis of human passengers (hereinafter patients). However as will be made clear, the invention is not limited to that. The apparatus allows the communication of medical diagnostic data from the aircraft A to a medical practitioner at a remote location B and for medical diagnostic advice and, if necessary, treatment advice to be transmitted from the remote location B to the aircraft. The medical data may be transmitted to one or more other locations C to obtain further advice.

The diagnostic apparatus comprises a plurality of medical sensors, including a battery powered ECG sensor array 1, a blood pressure sensor and pulse oximeter 3 which measures blood oxygen and pulse rate, and one or more other sensors such as a temperature sensor 2 and a capnometer 4. In the example shown in FIG. 1, the temperature sensor is an infra-red ear thermometer. The capnometer measures end tidal $CO_2$, respiration rate and other functions. The ECG sensor array is preferably a 12 lead array but could be a 4 lead array or be any other suitable ECG array. The ECG sensor array 1 produces many signals together having relatively high data rate. The other sensors have relatively low data rate (compared to the ECG array 1).

In a most preferred embodiment of the invention, the sensors comprise a 12 lead ECG sensor array 1, a blood pressure sensor and a pulse oximeter 3, a temperature sensor 2 and a capnometer 4 which are together considered by some experts to be essential for the reliable diagnosis of the seriousness of medical conditions of airline passengers.

The medical sensors are connected to a computer 6 comprising, in this example, a PC 104 processor (which is a known, standard, processor) having a Pentium (Trade Mark) 133 Mhz processor, 32 Mb RAM, 1 Gb hard drive, a video controller for a display device, 6 ports and a centralised power supply for all equipment. The PC runs for example the Microsoft Windows NT operating system (Microsoft, Windows and NT are Registered Trade Marks).

The combined blood pressure monitor and pulse oximeter, the thermometer 2, the ECG array and the Capnometer are connected to respective ports.

Also provided are: a microphone 7, a loudspeaker and/or earpiece 8, a digital camera 9, a head-up display 10, an LCD display 11, and a wrist pad 12 having keys for operating the apparatus.

The microphone 7, and earpiece 8 are preferably provided as a commercially available integral audio head-set for hands free operation. A small head-up display which also provides hand free operation is also commercially available. The digital camera may be wrist mounted together with the wrist pad also for ease of use.

Figure 5:
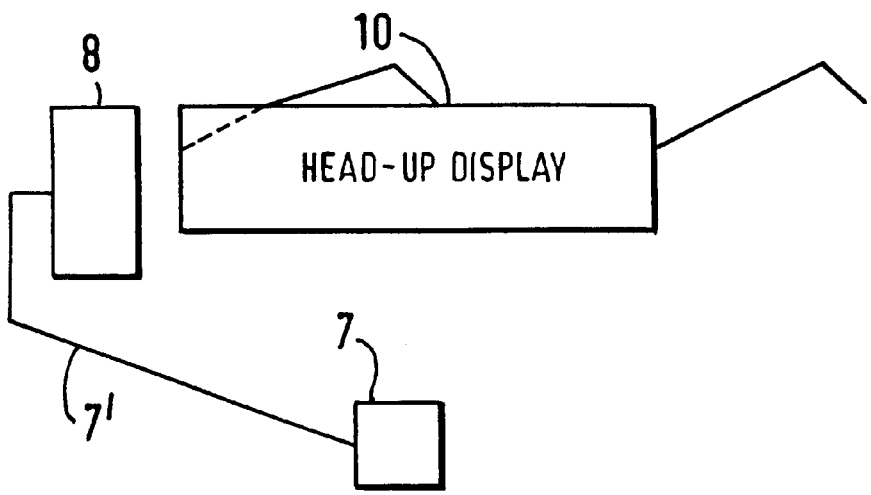
FIG. 5 is a schematic diagram of a head-up display and audio equipment for use by the operator of the apparatus of FIG. 1.

The headset comprising the microphone 7 and the earpiece 8 for hands free operation are currently considered essential to this embodiment of the invention: the head up display for hands free operation is a preferred but optional feature. Examples of the audio head set and head up display are shown in FIG. 5. Preferably the head set comprises a single ear-piece and the microphone 7 is mounted on a boom 71 to be adjacent the operators mouth for hands free use. The head-up display 10 in this example is mounted on a spectacle frame for hands free use. The spectacle frame may be provided by safety spectacles to protect the operator.

Figure 6:
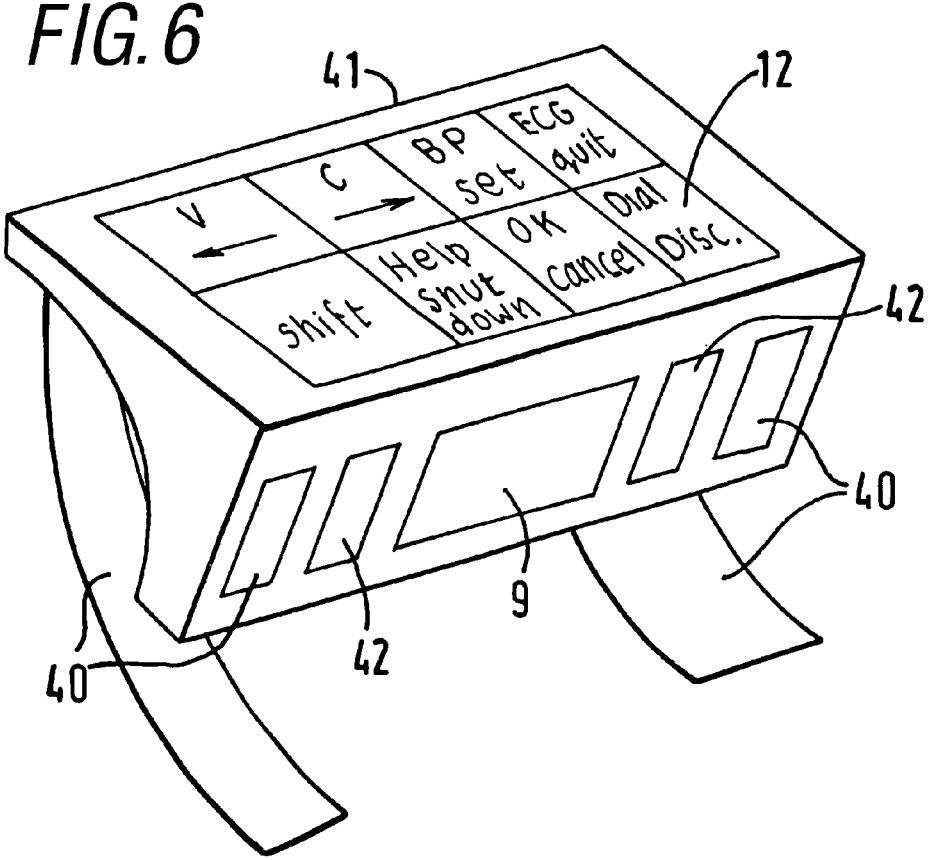
FIG. 6 is a schematic diagram of a wrist pad for use with the apparatus of FIG. 1.

The PC, in this example has no keyboard. Instead the operator is provided with a key pad 12 attached to his/her wrist by a strap 40 as shown in FIG. 6. The pad 12 has a minimum set of keys needed to operate the apparatus. In this example the keypad has 8 keys. Referring to FIG. 6 the keys comprise from top left to bottom right:- a video control key V; a capnometer control key C; a blood pressure monitor control key BP; an ECG control key ECG; a shift key; a help key; an OK key; and a Dial control key for initiating auto-dial. All the keys except the shift key have a shift level as follows:- Shift V is left arrow: shift C is right arrow: shift BP is set (the configuration of the Blood pressure monitor: shift ECG is quit (the ECG); shift help is shut down the whole system: shift OK is cancel: and shift Dial is disconnect.

The digital camera 9 is an optional but preferred feature. The camera 9 is preferably a digital video camera which provides moving images of the patient on the head up display and the LCD display 11 to provide a view finder action without needing to bring the camera to the operators eye. As will be described hereinafter, a still image is "grabbed" from the video for transmission, when required, to the medical expert at the remote location. A digital stills camera could in principle be used but is not currently preferred.

As shown by way of example in FIG. 6 the camera 9 is preferably housed in a wrist mounted housing 41 which also houses the keypad. The housing is shaped to match a persons wrist/forearm to which it is attached by Velcro (Registered Trade Mark) straps 40. The housing also has a holder 42 (shown schematically) for holding the head-up display. The keypad 12, the camera 9 and the head-up display 10 have respective cables which can be difficult to handle especially when initially retrieving them from the container (described hereinafter) in which they are stored and when the operator puts the wrist-mounted housing and head-up display on. The present inventor has discovered that handling of the wrist-mounted housing, the head-up display and the cables is considerably easier if the head up display is initially fixed to the wrist-mounted housing whilst that is retrieved from the container and whilst the housing is fixed to the wrist of the operator. The head-up display is then removed from the wrist mounted housing and put on the operators head.

The head-up display 10 and the LCD display 11 display the medical data produced by the medical sensors 1, 2, 3 and 4 as processed by the PC. The head-up display allows the operator to monitor the medical data. The LCD display 11 is provided to allow someone assisting the operator to monitor the data. In addition the head-up display and/or the LCD display are used to display operating instructions as will be discussed hereinafter.

The apparatus as so far described is coupled by two interfaces 14,171; 16,172 to two communications channels as will be described hereinafter. The interfaces provide in known manner isolation of the diagnostic apparatus and the aircrafts' communication network from each other. One interface 14,171 comprises a modem 14, which is used to transmit the medical data from the sensors 1 to 4 as processed by the PC 104. The processor 6 autodials via the modem 14 when so instructed by the operator to establish the communications link. Modem 14 provides the sensor data to one of the communications channels. In this case ECG data files, and still images from camera 9 are transmitted in batches. The modem 14 also provides transmission of the medical data from the other sensors 2, 3 and 4 in real time. The processor encodes the sensor data in TCP/IP format and the medical data from the ECG array 1 and from the camera 9 is transmitted as files using the FTP mode, in this example. Other modes of transmission are possible.

The other interface 16,172 is an audio interface controlled by the processor for providing two-way voice communication to and from the audio head-set 8 and 7. The processor 6 auto-dials, when so instructed by the operator, via the audio interface 16,172 when so instructed by the operator to establish the communications link. The interface could include a modem 16 which provides the auto-dial function under the control of the processor. In this example, the interfaces 14,171, 16,172 are connected to respective wireless transmitter/receivers 18 and 20 and also to telephone cords 601 and 602. The transmitter/receivers are preferably cordless telephones. An example is a CT2 cordless telephone. CT2 is a signal transmission/reception standard known from MPT 1334 and BS 6833. CT2 conforms to the common air interface and is a digital time division multiplex TDM system. The CT2 standard is approved for use in civil aircraft. It provides low-power, low range signals. However, other standards may be used such as CDMA which uses spread spectrum techniques. Most preferably cordless phones complying with the DECT standard are used at reduced power. The transmitter/receivers 18 and 20 communicate with corresponding cordless base stations 18', 20' coupled to a long range RF transmitter/receiver 26. In this example for use on aircraft, the long range transmitter/receiver 26 is part of communications satellite link (satcomms link) to a ground station 24 and the base stations 18' and 20' are coupled to the aircraft's CTU (Cabin Telephone Unit) 22 which interfaces with the satcomms link 26.

Some aircraft are equipped with an internal wired telephone network 30 with for example telephones 31 in the backs of seats or at least on bulkheads within the passenger areas in the aircraft. This allows the passengers and crew to make telephone calls via the CTU and the satellite link and the PSTN. The telephones are equipped with RJ45 telephone sockets 32 to allow other telephonic equipment to be connected to them. The cords 601 and 602 are provided for connecting to such sockets for connection via the CTU 22 to the satcomms link 26 Cordless base stations 18' 20' for use with the cordless phones would be plugged into the RJ45 sockets for coupling the cordless phones to the CTU. The interfaces 14,171 and 16,172 include circuits 171 and 172 which, in co-operation with the PC, automatically sense whether the cordless phones or the wired connections are in operation and route the signals to whichever is operative. The circuits 171 and 172 use high input impedance sensors to sense line voltage on the cords 601 and 602 without reducing the line voltage which would activate a connection. If a line voltage is detected a switch couples the modem 14 and the voice channel 16,7,8 to the CTU via the cords 601 and 602. If no line voltage is detected the cordless phones are actuated by default. Thus the operator simply plugs either the cords 601 and 602 or the cordless base stations into the aircrafts' wired telephone network 30 and the operator does not need to take any other action to activate the communications links except for initiating auto-dial. This allows use of the apparatus at the seat of the patient.

Figure 3:
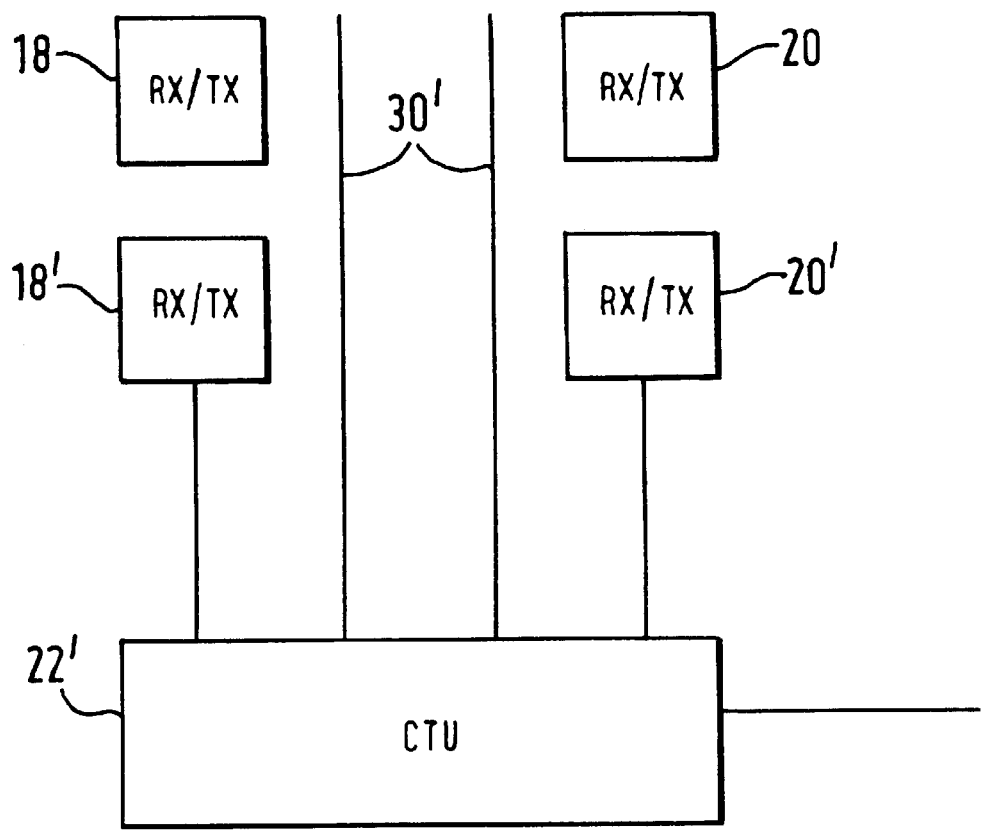
FIG. 3 is a block diagram of a modification of the apparatus of FIG. 1.
Figure 4:
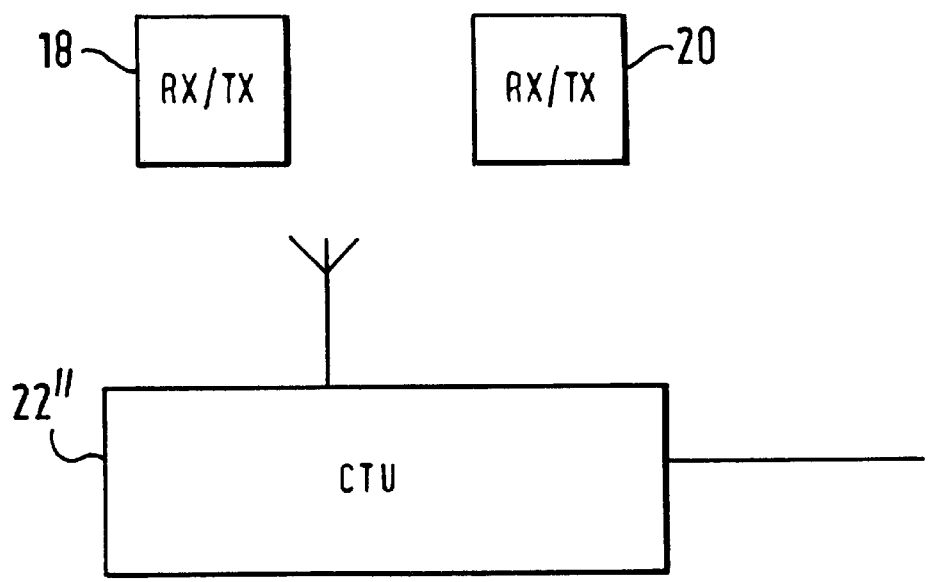
FIG. 4 is a block diagram of another modification of the apparatus of FIG. 1.

Various modifications which may be made to the foregoing arrangements are illustrated in FIGS. 3 and 4. Referring to FIG. 3, the diagnostic apparatus has two cordless transmitter/receivers 18 and 20. As schematically shown in the example of FIG. 3, an aircraft is equipped with a wired telephone system 30' connected to the CTU 22' for use by passengers and crew for two way telephone communication with the PSTN via the satcomms link 22. Passengers have corded phones not shown. In this example of the invention two ports of the CTU 22' have cordless base stations 18', 20' wired to them. The base stations 18' and 20' or the channels thereof may be provided by a single transmission/reception card which slots into a spare circuit board slot in the CTU. Thus the apparatus can be used anywhere on the aircraft without the need for corded connections As shown in the example of FIG. 4, some aircraft may be equipped with a wireless CTU 22". In this case the transmitter/receivers 18, 20 communicate directly with the CTU 22".

In the examples given above, two telephone channels are used which are standard telephonic voice channels available on an aircraft. The medical data, image signals and audio signals are multiplexed onto the channels with division of voice to one channel and data to the other.

The processor 4 is arranged, once operation is initiated, to automatically auto dial the telephone numbers of devices at the remote location B corresponding to the interfaces 14,16, 171,172 at the apparatus to establish the communications links. The numbers are auto dialled sequentially. The operator needs only to initiate auto dialling once the cords or the base stations are plugged into the aircrafts' telephone network.

In this example the ground station 24 at the remote location B is linked to the aircraft via the satcomms link and the public switched telephone network PSTN 26. At the remote location B a medical practitioner has an apparatus 28 corresponding to the apparatus on the aircraft for displaying the medical data, and the still images from the camera, and two way audio communications for talking to the operator on the aircraft. The medical data and images are viewed within respective windows on the ground display. The expert at location B preferably has the equipment necessary to transmit all the information received to a third party expert at another location via for example the internet, it being noted that the medical data is transmitted to the remote location according to TCP/IP and FTP which are standard protocols used on the internet.

Figure 2:
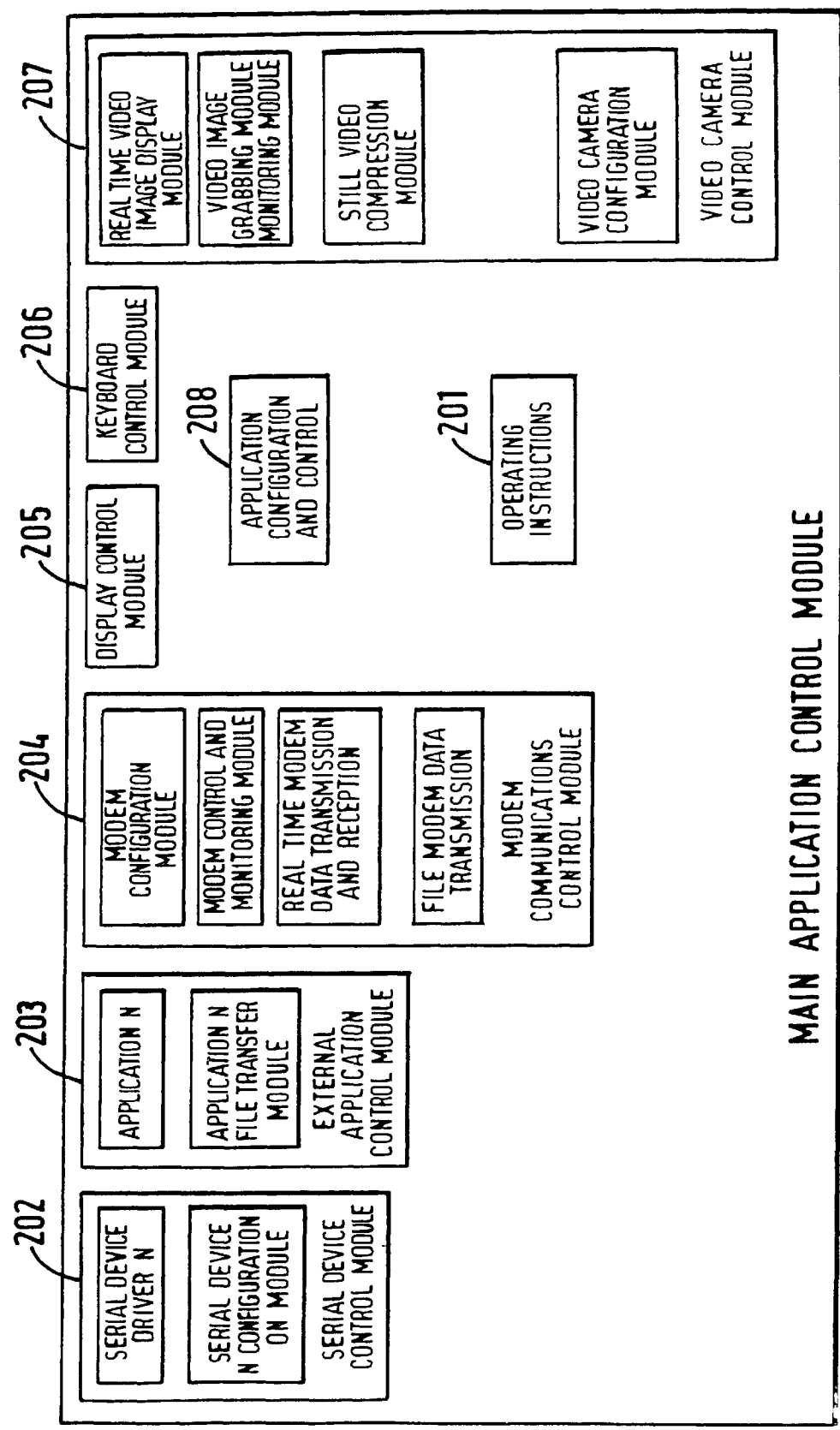
FIG. 2 is a schematic diagram of the organisation of the processor of the apparatus of FIG. 1.

Referring to FIG. 2 the software operated by the processor and which integrates the elements of the apparatus into a coherent system is schematically shown. The software is run within the WINDOWS NT (Trade Marks) operating system 200. The software comprises the following modules:

a) context sensitive operating instructions 201;
b) serial device control 202;
c) external application control 203;
d) communications control 204;
e) display control 205;
f) keyboard control 206;
g) camera control 207; and
h) application and configuration control 208.

The software will not be described herein in detail but its functions will be described in general terms. It is considered that where the software is not standard it is within the skill of a skilled programmer to implement the software.

Operating Instructions 201

Although the operator of the apparatus on the aircraft will be trained in its use and in the attachment of the sensors 1 to 4 to a patient, the need to use the apparatus will be infrequent and when needed will be in the event of a suspected medical emergency. Therefore the processor 6, when operation is initiated, displays on the head-up display 10 and/or the LCD display 11 context sensitive instructions for using the apparatus. For example, when the operator initially switches on the apparatus, instructions are automatically displayed showing how to connect the cordless base stations and the cords to the aircrafts' network and to initiate auto-dial. Instructions on how to put on the blood pressure monitor, and the pulse oximeter are then displayed. Details of how to put on the other sensors are displayed as those other sensors are selected. The instructions include instructions for attaching the sensors 1 to 4, especially the ECG sensor array if a standard 12 lead array is used: the electrodes need to be carefully and accurately attached to specific locations of the body.

Serial Device Control 202:

The sensors are coupled to ports to provide their medical data to the processor. However, preferably, the PC does not merely collect data from the sensors 2, 3 and 4 but also allows control of the sensor parameters. For example the sampling intervals of the sensors can be changed by the operator in response to instructions from the remote expert. The sensor parameters may be controlled by the expert at the remote location in some examples of the invention.

External Application Control 203:

ECG data is high bandwidth and requires processing to be displayed in an intelligible way. The ECG array has data compression software which compresses the files for transmission. Such software is standard and is supplied with the ECG array. However other compression techniques may be applied to the ECG data within the scope of the invention. The external application control controls the interfacing of that software with the other software modules of the diagnostic apparatus. When the remote medical expert calls for the use of the ECG array, the operator presses the appropriate key on the keypad which cause the display of instructions on how to fit the array. Pressing the key again causes the ECG data to be displayed in a window. The operator views the ECG data as it is displayed. Once the data is stable, pressing the key again causes 30 seconds of data to be displayed and stored on the PC 104 in a standard format and also transmitted automatically to the remote expert. The transfer of the ECG file may be initiated by the remote expert in some examples of the invention.

Communications Control 204

The communications control 204 causes the PC, interfaces 14,171 and 16,172 and cordless telephones 18, 20, to operate together to provide an efficient and easy-to-use data transmission/reception system for emergency medical diagnostic use on an aircraft.

The PC and interfaces 14,171, 16,172 provide for the automatic auto dialling of the communications channels upon initiation thereof by the operator. The PC preferably monitors the channels and, if a channel is lost, the PC automatically re-dials the channel without need for intervention by the operator. The PC warns the operator by displaying a warning on the screen that it is re-dialling.

The communications control also controls the configuration of the interfaces 14,171 and 16,172, especially of the interfaces 14,171 and 16,172.

The communications control co-operates with the external application control module 203 to transmit the ECG compressed data files automatically as batch files.

The communications control co-operates with the serial data control module 202 to transmit the real time sensor data from sensors 1, 2 and 3 and preferably also to allow the remote expert to reconfigure the sensors.

Display Control 205:

The display control controls the display of information on the head-up display and the LCD display panel 11.

Keyboard Control 206:

The keypad 12, as described above, is not a standard keyboard. This module 206 converts the data produced by the keypad to data which is used by the other modules.

Camera Control 207.

This module controls the configuration and operation (in conjunction with the keypad) of the digital video camera. It grabs a selected still image from the video, compresses the grabbed image and co-operates with the communications control module to automatically transmit the image to the remote expert. For example the video camera is activated by pressing the camera key on the pad once. The image is composed by the operator. Once the desired image is displayed pressing the key again compresses the image and automatically transmits it to the remote expert. The image may be compressed according to the JPEG standard but other compression techniques may be used.

Application Configuration and Control 208:

This module controls the interaction of the other modules with each other.

Figure 7:
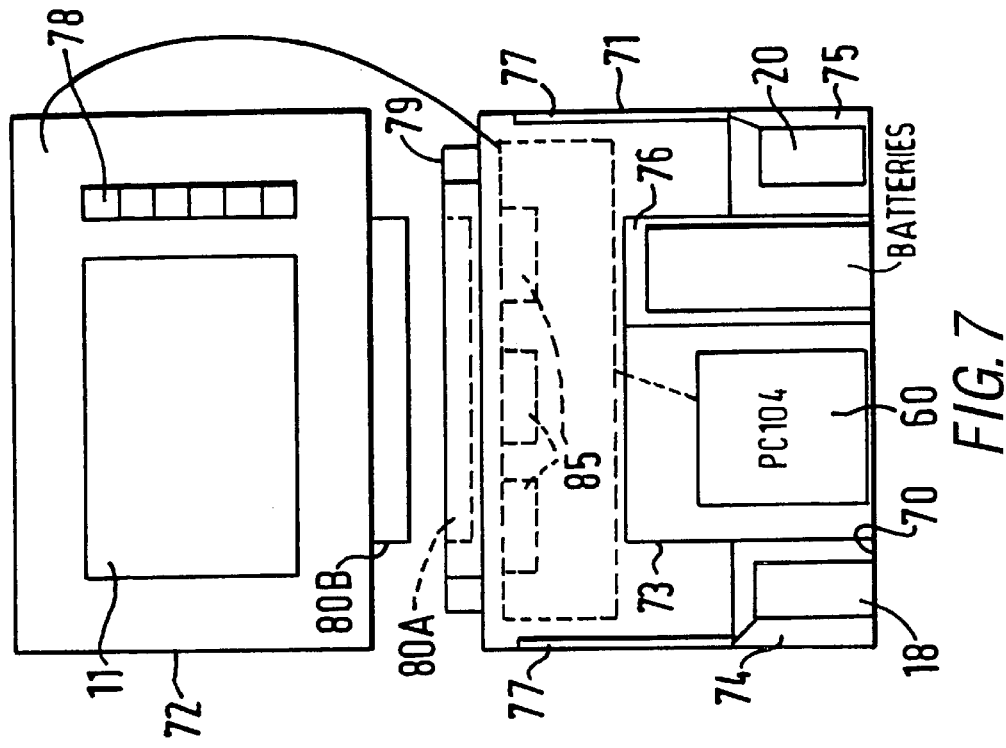
FIG. 7 is a schematic and simplified front view of a container for housing the apparatus.
Figure 8:
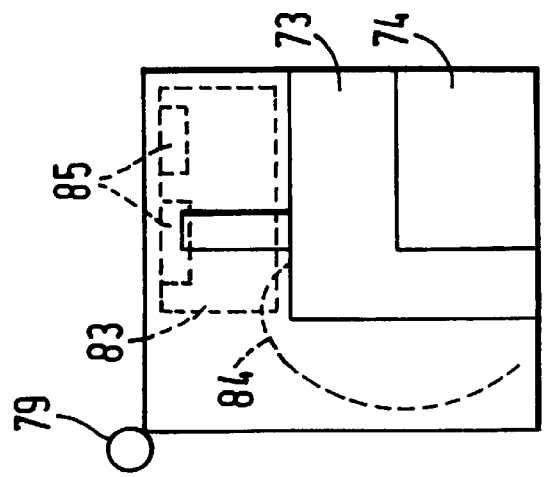
FIG. 8 is a side view of the container.
Figure 9:
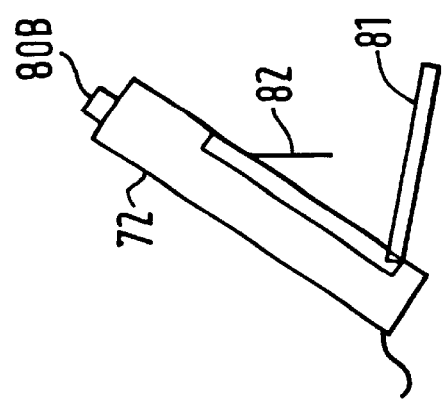
FIG. 9 is a side view of the lid of the container removed from the container.

In a preferred version of the invention, all the items shown in FIG. 1 are contained, when not in use, in a container, whereby the apparatus is portable. The preferred container has storage compartments for the audio head set, head-up display, the sensors, the PC and interfaces and other parts. The case contains batteries for operating the equipment contained in it. The preferred container will be described with reference to FIGS. 7 to 9. The container comprises an Aluminium base 70 fixed by e.g. screws to a body 71 and a lid 72 which is removably hinged to the body. The body and lid are preferably of moulded plastics e.g. of plastics foam with a solid skin. The PC is housed in a compartment 73, the cordless transmitter/receivers e.g. DECTs are in respective compartments 74 and 75, and batteries for powering the apparatus are in a compartment 76. These compartments 73 to 76 are defined between the Aluminium base as the floor thereof and ceiling members. The ceiling member of the PC compartment 73 comprises another Aluminium plate supporting electrical connectors. The ceiling members of the DECT compartments are integrally moulded. At least the compartments 73, 75 and 76 containing the PC and the DECTs are RF isolated, being internally coated with an electrically conductive coating which is electrically continuous with the Aluminium plates. The DECT compartments communicate with channels 77 moulded into the side walls of the body and which contain the antennae of the DECTs.

The lid 72 houses the LCD display panel 11 and may also house operating keys 78. The lid is hinged to the body by a hinge 79 and is held shut by a suitable latch (not shown). The hinge comprises a releasable connector having a part 80A hinged to the body and a part 80B fixed to the lid. The parts 80A and 80B releasably interlock. The lid has two supports 81 (only one shown in FIG. 9) hinged via a ratchet hinge to the lid and which support the lid when removed from the body. The lid also has a carrying handle 82. Thus the interlock of the two hinge parts 80A and B the latch and the handle must be sufficiently strong to safely carry the full container.

Above and behind the compartments 73 to 76 is a space 83 for containing the other parts of the apparatus. The space behind the compartments is intended to contain the cables (represented schematically by line 84) which link the PC and DECTs and batteries to the other parts, such as the sensors. The cables are attached to the items such as sensors, the head-up display and the keypad so that when an item is pulled out of the box the cable is pulled out with the item. Likewise when the item is replaced the cable is easily stowed again with the item. The space above the compartments contains a foam bed having in it depressions 85 for containing the sensors, the head-up display and the audio head-set and any other items. The depressions are preferably shaped to match the shapes of the respective items so that any one item can be stored in only one place and may also be labelled so that the items are correctly stored.

The batteries stored in the compartment 76 comprise rechargeable and non-rechargeable batteries. For initial use of the apparatus, the rechargeable batteries are used. If long term monitoring of a patient becomes necessary, the non-rechargeable batteries are used. This reduces the likelihood of having partially used non-rechargeable batteries. The PC 104 may monitor the state of the batteries and indicates on the head-up display their state. Both the rechargeable and the non-rechargeable batteries are provided with monitors having displays visible outside the container and actuable by e.g. a switch outside the container to indicate the state of the batteries when the apparatus is not in use. The indicator may comprise a red LED for indicating that the batteries need immediate replacement, an orange LED for indicating replacement is due soon and a green LED for indicating fully charged batteries. Flight crew can then easily check the batteries before each flight without booting up the apparatus which is very wasteful of battery life. An on-off switch is provided for powering the apparatus for use. The apparatus automatically boots up when switched on.

Various modifications may be made to the apparatus. The PC and the communications system may also allow the diagnostic apparatus itself to be monitored from the remote location to detect faults and arrange maintenance when it is not in use The whole apparatus may be wearable. That is, in addition to the audio head set and the head up display worn on the operators head, the processor 6 may be attached to the operators body by a suitable harness for example. The LCD display 11 may be replaced by another suitable type of display. The video camera 9 may be replaced by or supplemented by a stills camera. In principle more telephone channels could be provided: for example 3 channels could be provided. The audio head set and the head up display and optionally also the camera may be provided in a single head assembly such as a helmet.

A normal keyboard may be provided in examples of the invention. If the keyboard is used, it may be used in addition to or as an alternative to the voice communications for the exchange of information with the medical practitioner, the alphanumerics produced by the keyboard being transmitted via one of the interfaces 14 and 16. A printer may be provided as part of the apparatus.

The case may contain medical stores. The case is preferably stored in a rack in the aircraft. The rack may be equipped with a battery charging supply which the case engages when stored to keep the charge on the rechargeable batteries replenished. The case may have a sensor to sense when it is removed from the battery charging supply or from the rack. When cordless phones are provided, the PC may then respond to the sensor to immediately "boot-up" and begin auto-dialling the communications channels to connect the apparatus with the remote location as soon as the case is removed from the rack so that when the operator opens the case at the patient, the system is operational.

Although the invention has been described by way of example with reference to satcomms links it is not limited to such links. In some parts of the world ground based communications systems communicate with aircraft in flight and such systems may be used. Although the invention has been described with reference to a human patient it could be applied to other mammals or animals. If applied to other mammals or animals, instead of communicating with a doctor, communication would be with a veterinary expert.

The preferred emdobiment of the invention allows the apparatus to be used at the seat of a patient on an aircraft. The corded connections and preferably the cordless phones allow simple connection to the aircrafts' communication system anywhere on an aircraft. The wrist mounted keypad, the audio head set and the head-up display allow the apparatus to be used in cramped conditions. The provision of the camera in the wrist mount assists-use of the apparatus in such cramped conditions. Attaching the head-up display to the wrist mount simplifies the set-up of the apparatus for use in such conditions and simplifies the handling of the cables by the operator. The apparatus is arranged to be as simple as possible for the operator to use.

What is claimed is:

1. Diagnostic Apparatus comprising:
   a plurality of sensing means (1–4) for sensing data of a body;
   means (7,8) for producing and reproducing voice signals, the producing and reproducing means being arranged to be used by an operator hands-free;
   a first communications means (14,20) coupled to the producing and reproducing means, and a second communications means (16,18);
   display means (11); and
   processing means (6) arranged to
      i) process the data, ii) display the processed data on the display means (11), iii) control the first and second communications means to automatically establish respective links to a remote location, and iv) supply the processed data to the second communications means;
      the apparatus being arranged so that in use two-way voice communication is established between the said operator and an expert at the remote location and the sensed data is transferred to the remote location via the second communications link to allow the said expert to diagnose a condition of the body and to communicate the diagnosis to the said operator.

2. Apparatus according to claim 1, wherein the processor encodes the sensed data according to TCP/IP for transmission.

3. Apparatus according to claim 1, which is medical diagnostic apparatus, wherein the said sensing means are medical sensing means.

4. Apparatus according to claim 3, wherein the medical sensing means include an ECG array.

5. Apparatus according to claim 4, wherein the ECG array is a twelve lead array.

6. Apparatus according to claim 4, wherein the processor organizes the ECG data into a file and transfers the file using File Transfer Protocol (FTP).

7. Apparatus according to claim 3, wherein the medical sensing means include a capnometer.

8. Apparatus according to claim 3, wherein the medical sensing means include a temperature sensor.

9. Apparatus according to claim 8, wherein the temperature sensor is an infra red ear thermometer.

10. Apparatus according to claim 3, wherein the medical sensing means include a blood pressure sensor.

11. Apparatus according to claim 3, wherein the medical sensing means include a pulse oximeter.

12. Apparatus according to claim 3, wherein the medical sensing means include a combined blood pressure sensor and pulse oximeter.

13. Apparatus according to claim 1, wherein the voice signal producing and reproducing means comprises a headset including a microphone and at least one ear-piece.

14. Apparatus according to claim 1 wherein the first and second communications means each include a low power wireless transmission and reception means.

15. Apparatus according to claim 14, wherein each low power wireless transmission and reception means comprises a CT2 or DECT device or a spread spectrum device such as a CDMA device.

16. Apparatus according to claim 14, comprising interface means (14,171, 16,172) for supplying the processed data to the low power transmission and reception means.

17. Apparatus according to claim 16, wherein the interface means (14,16, 171,172) each further include autodialling means controlled by the said processor for establishing the said links to the remote location via the PSTN.

18. Apparatus according to claim 17, wherein the interface means comprises modem means for supplying the processed data to the low power wireless transmission and reception means.

19. Apparatus according to claim 16, wherein the interface means each include cords (601,602) for connection to respective wired communications channels (30).

20. Apparatus according to claim 19 wherein the interface means further includes means (171,172) for sensing which one of the corded connection to the wired communications channels and the said wireless transmission and reception means is operative and for supplying the voice signals and the processed data to the operative one.

21. Apparatus according to claim 14, in combination with a long range transmission/reception apparatus coupled to the said low-power receiver/transmitter means for re-transmitting at least the sensed data and the voice signals to the remote location and for receiving at least the voice signals from the remote location.

22. Apparatus according to claim 1, wherein the said display means comprises a head-up display.

23. Apparatus according to claim 22, wherein the said display means comprises a further display (11).

24. Apparatus according to claim 1, further comprising a camera for producing image signals representing the said body, the processing means being arranged to process the image signals and to supply the processed signals to the said second communications means.

25. Apparatus according to claim 24, wherein the camera is an electronic camera.

26. Apparatus according to claim 24, wherein the processor encodes the image data according to TCP/IP for transmission.

27. Apparatus according to claim 26, wherein the processor organizes the image data into a file and transfers the file using the File Transfer Protocol (FTP).

28. Apparatus according to claim 1, further comprising a key-pad for controlling the apparatus.

29. Apparatus according to claim 28, wherein the key-pad is arranged to be mounted on the wrist of the said operator.

30. Apparatus according to claim 1, housed in a container the container comprising at least one compartment containing the processor and the first and second communications means and at least one other compartment containing at least the sensing means, and the producing and reproducing means.

31. Apparatus according to claim 30, wherein the said at least one other compartment also contains a head-up display.

32. Apparatus according to claim 30, wherein the container has a lid and the said splay means is housed in the lid.

33. Apparatus according to claim 30, wherein the said at least one compartment is RF screened.

34. Apparatus according to claim 30, wherein the base of the container is heat sink which provides the floor of the said at least one compartment, the processor being thermally coupled to the heat sink.

35. Apparatus according to claim 30, wherein the first and second communication means have antennae and are contained in at least one further RF screened compartment and the antennae thereof extend outside the said RF screened compartment.

36. Apparatus according to claim 30 which is battery powered.

37. Apparatus according to claim 36, comprising rechargeable and non-rechargeable batteries for powering the apparatus.

38. Apparatus according to claim 36, wherein the batteries are contained in yet further compartments in the container.

39. Apparatus according to claim 1, further comprising means for monitoring the condition of the apparatus, the wireless transmission/reception means being arranged to transmit to the remote location date relating tot he condition of the apparatus.

40. Apparatus according to claim 1, wherein at least some of the sensing means are configurable and/or actuable via the wireless transmission/reception means from the remote location.

41. Apparatus according to claim 1, comprising a power switch, the processor being arranged to assume its operating condition automatically in response to switching-on the apparatus at the power switch.

42. A portable diagnostic apparatus comprising a container containing:
   a) a plurality of sensing means (1–4) for sensing data of a body
   b) means (7, 8) for producing and reproducing voice signals, the producing and reproducing means being arranged to be used by an operator hands-free,
   c) display means (11);
   d) first communication means (14, 20) coupled to the voice signal producing and reproducing means;
   e) second communication means (16, 18);
   f) processing means (6) to which the said sensing means, voice signal producing and reproducing means, display means and first and second communication means are connected to form an integrated system, the processing means being arranged to
      i) control the sensing means
      ii) process the said sensed data,
      iii) display the processed data on the display means
      iv) control the first and second communication means to automatically establish respective first and second communication channels to a remote location, and
      v) display context-sensitive operating instructions on the display means;
      the first channel coupling the voice signals to the remote location and the sensed data being coupled to the remote location via the second channel;
      wherein the container has at least one compartment, at least one other compartment, and a lid, the processing means and the first and second communication means (14, 20; 16, 18) are contained in the said at least one compartment of the container, the said at least one other compartment contains at least the sensing means and the producing and reproducing means, and
      the said display means is housed in the lid, the lid being separable from the container.

* * * * *